United States Patent
Hasler-Nguyen et al.

(10) Patent No.: US 7,452,549 B2
(45) Date of Patent: Nov. 18, 2008

(54) SYNERGISTIC ANTIOXIDANT COMBINATION OF DELTA TOCOLS AND POLYPHENOLS

(75) Inventors: Nathalie Hasler-Nguyen, Le Muids (CH); Jacob Zijlstra, Coppet (CH); John P. Troup, Commugny (CH)

(73) Assignee: Nestec S.A., Vevey (CH)

( * ) Notice: Subject to any disclaimer, the term of this patent is extended or adjusted under 35 U.S.C. 154(b) by 578 days.

(21) Appl. No.: 10/399,339

(22) PCT Filed: Oct. 22, 2001

(86) PCT No.: PCT/EP01/12188

§ 371 (c)(1), (2), (4) Date: Jul. 24, 2003

(87) PCT Pub. No.: WO02/34072

PCT Pub. Date: May 2, 2002

(65) Prior Publication Data

US 2004/0023894 A1    Feb. 5, 2004

(51) Int. Cl.
*A61K 47/00* (2006.01)
*C11B 5/00* (2006.01)
(52) U.S. Cl. .................. 424/439; 424/401; 426/541
(58) Field of Classification Search .................. None
See application file for complete search history.

(56) References Cited

U.S. PATENT DOCUMENTS

| | | | |
|---|---|---|---|
| 3,852,502 A | 12/1974 | Bishov et al. | |
| 5,217,992 A | 6/1993 | Wright et al. | |
| 5,348,974 A | 9/1994 | Wright et al. | |
| 5,788,971 A | 8/1998 | Togasaki | |
| 6,231,877 B1 | 5/2001 | Vacher et al. | |
| 6,239,114 B1 | 5/2001 | Guthrie et al. | |
| 6,375,992 B1 * | 4/2002 | Blumenstein-Stahl et al. | 424/729 |
| 6,814,958 B1 * | 11/2004 | Sekimoto | 424/58 |

FOREIGN PATENT DOCUMENTS

| | | |
|---|---|---|
| AU | 200013476 A1 | 1/2000 |
| EP | 0 962 150 | 12/1999 |
| EP | 1 044 687 | 10/2000 |
| EP | 1044687 A1 * | 10/2000 |
| GB | 2 259 014 | 3/1993 |
| GB | 2 343 101 | 5/2000 |
| JP | 60214864 | 10/1985 |
| JP | 01242689 | 9/1989 |
| JP | 02055785 | 2/1990 |
| JP | 5320036 | 12/1993 |
| JP | 06145062 | 5/1994 |
| JP | 07255436 | 10/1995 |
| JP | 08023922 | 1/1996 |
| WO | WO 96/19218 | 6/1996 |
| WO | WO 99/15167 | 4/1999 |
| WO | WO 9915167 A2 * | 4/1999 |
| WO | WO 00/15201 | 3/2000 |
| WO | WO 00/57876 | 10/2000 |
| WO | WO 00/72862 | 12/2000 |
| WO | WO 01/51043 | 7/2001 |

OTHER PUBLICATIONS

Chen et al., "Protection by Multiple Antioxidants Against Lipid Peroxidation in Rat Liver Homogenate", Lipids, vol. 31, No. 1, pp. 47-50, (1996).
Hodgson et al., "Acute effects of ingestion of black and green tea on lipoprotein oxidation", Am. J. Clin. Nutr., vol. 71, pp. 1103-1107, (2000).
Kagan et al., "Recycling of Vitamin E in human low density lipoproteins", Journal of Lipid Research, vol. 33, pp. 385-397, (1992).
Lee, C., "Antioxidant ability of caffeine and its metabolites based on the study of oxygen radical absorbing capacity and inhibition of LDL peroxidation", Clin Chim Acta, vol. 295, No. 1-2, pp. 141-154, (2000).
Mortensen et al., "Relative stability of carotenoid radical cations and homologue tocopheroxyl radicals. A real time kinetic study of antioxidant hierarchy", FEBS Letters, vol. 417, pp. 261-266, (1997).
Nanjo et al., "Effects of Dietary Tea Catechins on α-Tocopherol Levels, Lipid Peroxidation, and Erythrocyte Deformability in Rats Fed on High Palm Oil and Perilla Oil Diets", Biol. Pharm. Bull. vol. 16, No. 11, pp. 1156-1159, (1993).
Packer, L., "Interactions among Antioxidants in Health and Disease: Vitamin E and Its Redox Cycle", Vitamin E in Health and Disease—Department of Molecular and Cell Biology, University of California at Berkeley, Berkeley, California, 99. 271-275, (1992).
Pearce et al., "Hypocholesterolemic Activity of Synthetic and Natural Tocotrienols", J. Med. Chem., vol. 35, pp. 3595-3606, (1992).
Pietta et al., "Dietary Flavonoids and Interaction with endogenous antioxidants", Biochemistry and Molecular Biology International vol. 44, No. 5 pp. 1069-1074, (1998).
Qureshi et al., "Response of Hypercholesterolemic Subjects to Administration of Tocotrienols", Lipids, vol. 30, No. 12 pp. 1171-1177, (1995).
Qureshi et al., "Novel tocotrienols of rice bran modulate cardiovascular disease risk parameters of hypercholesterolemic humans", J. Nutr. Biochem., vol. 8, pp. 1-9, (May 1997).
Tijburg et al., "Effects of green tea, black tea and dietary lipophilic antioxidants on LDL oxidizability and atherosclerosis in hypercholesterolaemic rabbits", Atherosclerosis, vol. 135, pp. 37-47, (1997).
Zhu et al., Regeneration of α-Tocopherol in Human Low-Density Lipoprotein by Green Tea Catechin, J. Agric. Food Chem., vol. 47, No. 5, pp. 2020-2025, (1999).
MaxiLife Products Polypheolics, Inc., The Synergism Between Grape Seed Extract and Vitamin C and E, MegaNatural Gold, Jul. 10, 2000.
International Search Report.

* cited by examiner

*Primary Examiner*—S. Tran
(74) *Attorney, Agent, or Firm*—Gary M. Lobel

(57) ABSTRACT

A source of δ-tocotrienol and/or-tocopherol acts synergistically with an antioxidant source comprising polyphenols, to effect suppression of LDL oxidation in serum. The combination of these two antioxidant sources has wide-ranging applications in treatment of medical conditions arising from free radical generation, including arteriosclerosis and cancer.

18 Claims, 5 Drawing Sheets

SYNERGISTIC ANTIOXIDANT COMBINATION OF DELTA TOCOLS AND POLYPHENOLS

FIELD OF THE INVENTION

The present invention relates to compositions comprising a combination of at least one source of δ-tocols (tocotrienol and/or tocopherol), with an antioxidant source comprising polyphenolic compounds. Due to synergistic effects, such compositions are useful in treating or preventing disorders caused by free radicals, such as those relating to coronary heart disease, cancer and rheumatism.

BACKGROUND OF THE INVENTION

There is ample evidence suggesting that diets rich in fruit and vegetables protect against the development of chronic illnesses such as Coronary Heart Disease (CHD) and cancer, which are the major killer diseases among affluent populations. It has been recognized for some time that these beneficial effects are due, at least in part, to the antioxidant components of these foodstuffs, which can inhibit cellular damage by free radicals. In the body, free radical damage arises due to reactive oxygen species (ROS) being formed endogenously within the tissues, and also as a result of exposure to radicals arising from cigarette smoke, ionising radiation, air pollution and other environmental insults. These free radicals have the potential to interact with biological molecules such as proteins, lipids and DNA, and they are implicated in the aetiology of diverse diseases.

Antioxidants are likely to come into play in many aspects of multi-factorial disease conditions such as cancer or CHD, so it is difficult to establish how their primary effects are exerted. However, in the case of the process of atherogenesis a clear link has been demonstrated between oxidation of low density lipoprotein (LDL) and the formation of occlusive plaque in the arteries. Vitamin E (α-tocopherol) consumed as part of the diet is naturally present in the blood, where it acts to spare the LDL from oxidation. In vitro experiments have established that other natural sources of antioxidants, such as green tea, can also significantly retard the oxidation of LDL. In vivo studies have confirmed the in vitro tests, showing that increasing dietary intakes of some antioxidants, such as Vitamin E, can increase the resistance of LDL to oxidation and thereby reduce lesions in the arteries.

The main antioxidants from dietary sources are vitamins E (α-tocopherol) and C (ascorbic acid), the carotenoids, and polyphenols. Due to an increase in public awareness of the importance of these micronutrients, it has become commonplace for people to supplement their diets with natural or synthetic antioxidant sources. However, in spite of this general shift in favour of healthier eating patterns the incidence of CHD and cancer continues to be concerning.

It is clearly easier to encourage the use of dietary antioxidant supplements than to induce radical changes in the diet. But dietary supplements have their own drawbacks, particularly since there are detrimental side effects associated with high doses. Recently, for instance, the US Institute of Medicine advised that the upper limit of intake of vitamin E should be set at 1000 mg α-tocopherol per day, because of the risk of stroke and uncontrolled bleeding due to the anti-coagulant properties of this nutrient. β-carotene has actually been linked to an increase in the incidence of cancer. Thus, at the maximum safe dosage the antioxidant effect may be less than optimal.

Consequently, there is a need for new antioxidant products, which can be provided in the form of a food or as a dietary supplement, and which are potent in preventing CHD, cancer and other diseases associated with free radical generation, at dosages which do not pose health risks.

SUMMARY OF THE INVENTION

According to a first aspect of the present invention there is provided a composition comprising a mixture of:
(a) a source of δ-tocol comprising greater than 2% by weight δ-tocol; and
(b) polyphenols, with the proviso that when (b) comprises citrus flavonoids, (a) comprises δ-tocopherol.

In some embodiments, the composition may further comprise α-tocopherol, wherein a weight ratio of δ-tocol to α-tocopherol is greater than 0.65.

In a second aspect of the invention there is provided a composition comprising in a daily dosage:
(a) at least 5 mg δ-tocopherol or of a mixture of δ-tocotrienol and δ-tocopherol; and
(b) polyphenols.

In another aspect of the invention there is provided a composition comprising in a daily dosage:
(a) at least 5 mg of δ-tocotrienol; and
(b) polyphenols other than citrus flavonoids.

In a further aspect of the invention there is provided a food or beverage product comprising:
(a) a source of δ-tocol comprising greater than 2% by weight δ-tocol; and
(b) an antioxidant source comprising polyphenols, and optionally one or more of carbohydrate, fat, fibre and protein.

In yet another aspect of the invention there is provided a pharmaceutical composition or dietary supplement comprising the composition of the invention as claimed, with a pharmaceutically acceptable carrier.

In another aspect of the invention there is provided use of a composition according to the invention as claimed, as a scavenger of free radicals.

In a further aspect of the invention there is provided use of a composition comprising a mixture of:
(a) a source of δ-tocol preferably comprising greater than 2% by weight δ-tocol; and
(b) an antioxidant source comprising polyphenols, as a preservative for preventing spoilage of food and beverage products.

In a further aspect of the invention there is provided a composition according to the invention as claimed, for use as a medicament.

In yet another aspect of this invention there is provided use of a composition according to the invention as claimed, in the manufacture of a medicament or nutritional formulation for the prevention or treatment of a disease condition or corporal damage associated with the generation of free radicals.

In another aspect of the invention there is provided a kit comprising:
(a) a source of δ-tocol preferably comprising greater than 2% by weight δ-tocol; and
(b) an antioxidant source comprising polyphenols, for separate, sequential or simultaneous administration.

In a further aspect of the invention there is provided a cosmetic composition comprising:

(a) a source of δ-tocol preferably comprising greater than 2% by weight δ-tocol; and
(b) an antioxidant source comprising polyphenols; and
(c) a cosmetic base.

DETAILED DESCRIPTION OF THE INVENTION

Figure 1:
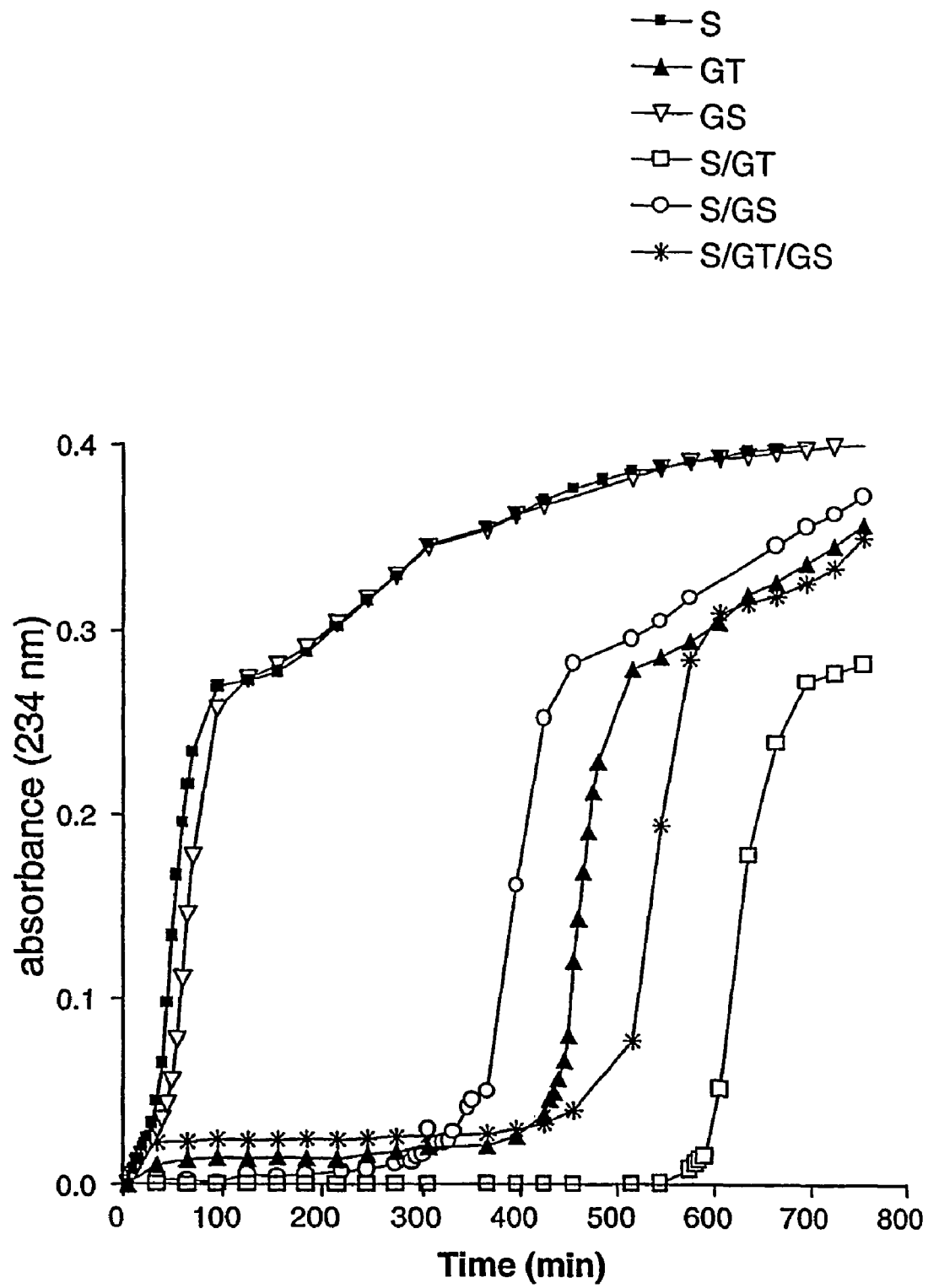
FIG. 1 is a graph illustrating the effects of TRF from palm oil (S; Sugro), green tea extract (GT), and grape seed extract (GS), and combinations thereof, on the lag phase in an in vitro LDL oxidation assay.

It has surprisingly been found that the antioxidant properties of a combination of a tocol source comprising δ-tocotrienol and/or -tocopherol, with an antioxidant source comprising polyphenols, are more than additive, i.e. we have observed a synergistic effect in preventing oxidation in an in vitro LDL oxidation model (which is a representative model for free radical oxidation in vivo in general, and peroxidation of lipids in particular).

As a result of this synergy, it is possible to obtain an equivalent or improved antioxidant effect at lower dosages compared with conventional antioxidant products. This has the advantage that a powerful antioxidant effect can be achieved in vivo while avoiding the need to ingest any single antioxidant at levels that could threaten health. In addition, the maximum antioxidative benefit obtainable is superior to the maximum benefit obtainable through use of these antioxidants separately.

Tocopherols and tocotrienols (sometimes collectively known as vitamin E, or "tocols") are fat-soluble biological membrane components that are structurally-related, having the same aromatic chromanol "head". Whereas tocopherols have a saturated isoprenoid side chain, tocotrienol side chains are unsaturated. Tocols are found in α (alpha), β (beta), γ (gamma) and δ (delta) forms, classified according to the position of substitution on the phenol ring. In the context of the present invention the generic term "tocol" is used to refer to any isomer of tocotrienol or tocopherol or salt form thereof, or any mixture (racemic or otherwise) of such molecules. "δ-tocols" are a sub-group of these tocols, i.e. those having a δ-monomethyl group on the benzene ring of the chroman moiety, and this term is intended to refer to any isomer of δ-tocotrienol or δ-tocopherol or salt form thereof, or any mixture (racemic or otherwise) of such molecules. Chemical derivatives and homologues of tocols are also acceptable for use in the invention, including tocol esters such as the acetate, succinate and palmitate.

The compositions of the invention comprise at least one source (a) of δ-tocotrienol and/or δ-tocopherol, and are preferably rich in these δ-tocols, the δ-tocotrienol content or δ-tocopherol content or δ-tocol content of the δtocol source preferably being at least 0.1% by weight of the source, preferably at least 1%, more preferably greater than 2%, most preferably at least 7%, and optionally at least 9%, by weight of the source.

In another embodiment of the invention the δ-tocol content of the δ-tocol source (a) is at least 25% by weight, and preferably at least 50% by weight of that source. Optionally the tocol component of the composition consists essentially of (e.g. at least 90%, preferably at least 95% by weight of), or consists of, δ-tocotrienol and/or δ-tocopherol. Individual or mixed δ-tocols can be obtained in substantially pure form (e.g. ≧90% purity, preferably ≧95% purity) by chemical synthesis or by purification from natural sources, according to conventional procedures.

Tocol sources which are especially rich in δ-tocols include cereals (barley, oats, rice, wheat, rye, amaranths) and plant oils, such as rice bran oil, barley oil, olive oil and palm oil. The source may be enriched in δ-tocols by conventional processing means, such as that disclosed in WO 91/17985. Preferred sources of δ-tocols for use in the invention are the Tocotrienol Rich Fractions (TRF; e.g. Nutriene®, TocoTab P40®, GoldTriE®, Palmvitee®,), obtained by molecular distillation from any of the above-named plant oils. Normally, the δ-tocol source, which may be a fraction or extract, will comprise a mixture of fat-soluble molecules, including a range of tocopherols and tocotrienols. Optimally, the total tocol content of the tocol source is at least 30% by weight, preferably at least 50% by weight, and most preferably at least 70% by weight of the source. In order to reach this concentration of tocols it may be necessary to further concentrate commercially available tocol products such as TRF.

In one embodiment of the invention the weight ratio of total tocotrienols to α-tocopherol in the composition is greater than 0.5, preferably greater than 1.0, or even greater than 2.0 or 3.0. Optionally, the composition is substantially free of α-tocopherol, meaning that less than 5%, preferably less than 2% by weight of the total tocol content is α-tocopherol.

In a particularly preferred embodiment, source (a) is selected on the basis that the weight ratio of δ-tocol to α-tocopherol is greater than 0.65, preferably at least 1.0. One such source is TocoTab P40® (Fuji), a TRF prepared from palm oil by a process which selectively enriches in δ-tocotrienol. As an example of a δ-tocol source with a very high ratio of δ-tocol to α-tocopherol (>1.5), Covi-Ox™T-30 P (a mixture of tocopherols sold by Cognis GmbH), may be mentioned. By selecting source (a) to have a high ratio of δ-tocol to α-tocopherol it is possible to ingest a relatively large dose of antioxidant δ-tocols without the risk of exceeding the maximum daily intake of α-tocopherol recommended by national health authorities.

Suitable daily doses of total tocol in the composition of the invention are up to 2000 mg, preferably 5 to 1000 mg, and optimally in the range of 50 to 500 mg, generally 100-300 mg. In a unit dosage, the composition of the invention preferably comprises 0.1 to 50 mg, more preferably 0.25 to 20 mg, and most preferably 0.5 to 15 mg δ-tocol. The preferred daily dosages of δ-tocol are up to about 1000 mg, optionally 0.1 to 500 mg, more preferably 0.25 to 125 mg, usually 0.5 to 60 mg, and optionally 5 to 25 mg. Where TRF is used as the source (a) of δ-tocol it is preferably consumed in an amount of 10 to 500 mg/day, more preferably 50-250 mg/day, and most preferably 20-100 mg/day. In terms of body weight, an appropriate daily dosage range is about 5 μg to 5 mg δ-tocol/kg, especially about 0.1 to 2 mg δ-tocol/kg. The daily dosage may correspond to a single unit dosage, or may be provided through multiple unit dosages.

Although remarkable synergistic effects are observed with each of δ-tocotrienol and δ-tocopherol, the former performs marginally better in in vitro LDL oxidation studies, and therefore can be administered in lower doses to achieve the same effect. Therefore an optimal composition according to the invention will comprise &tocotrienol, in the presence or absence of other tocols.

Antioxidant source (b) of the composition of the invention can be defined as comprising at least one source or substance comprising polyphenolic compounds. These polyphenolics contribute to the exceptional antioxidant activities of sources (a) and (b) when used in combination.

In antioxidant source (b) there may be a single polyphenolic source or mixtures of different polyphenolic sources. The term "polyphenol" can be defined as a compound which possesses an aromatic ring bearing one or more hydroxy substituents, including functional derivatives. Antioxidant agents containing polyphenols include plant, algal or fungal extracts or fractions rich in polyphenols, including flavonoids (isoflavones, anthocyanins, proanthocyanidins and anthocyanidins, flavans, flavonols, flavones and flavanones). Specific examples of bioflavonoids are catechins (catechin, epicatechin, gallocatechin, epigallocatechin, epicatechin gallate, epigallocatechin gallate), quercetin, rutin, hesperidin and genistein.

Chemically synthesized or purified polyphenols and mixtures thereof may be used in place of plant extracts. Polyphenols may be synthesized or extracted from natural sources by any suitable method known to those skilled in the art, particularly using food-grade solvents. Liquid and solid (e.g. granulate or powder form) extracts are suitable.

As a rule, the greater the content of polyphenols in the extract the larger the synergistic effect observed. Therefore in one embodiment of the invention the antioxidant source (b) used in the invention is rich in polyphenols, i.e. having a polyphenol content of at least 50% by dry weight, preferably at least 65% by dry weight, and optionally at least 75% by dry weight of source (b). Antioxidant source (b) may consist essentially of polyphenols.

In particular, herbal infusions, teas, tisanes and extracts (e.g. lyophilised extracts) made from leaves of various sorts are acclaimed for their polyphenol-associated free-radical scavenging effects. Herbal sources from which antioxidant preparations can be made include materials obtained from: tea (*Camellia sinensis* and *Camellia assaimica*), rooibos, honeybush, *Ginkgo biloba, Phyllanthus* species, *Catechu gambir, Urtica* species, rosemary, sage, mint, etc. *Camellia sinensis* leaves are especially preferred. Green tea is particularly potent, as is red tea, white tea and Mohnai tea, but black tea, Oolong tea, yellow tea and jasmine tea may also be used. All varieties of Pu Erh teas and green teas are preferred. Where the source of polyphenols is leaf material, this material may be freshly-gathered leaves, fresh leaves that are dried immediately after gathering, fresh tea leaves that have been heat treated before drying to inactivate any enzymes present, unfermented tea, fermented tea, instant tea, tea solids, partially fermented tea leaves, and hot or cold aqueous and alcoholic extracts (tinctures) of these leaves, and mixtures thereof.

Polyphenols naturally occurring in *Camellia* plants and extracts therefrom are especially preferred for use as component (b) in the compositions of the invention. Included in this group of polyphenols are the catechins, namely epicatechin, epigallocatechin, epicatechin gallate, and epigallocatechin gallate. Sugar salts, sugar esters and other edible physiologically available derivatives of catechins may substitute for the naturally-occurring forms.

Effective extracts (e.g. aqueous or alcoholic) as a source of antioxidant (b) can be obtained from plant parts including leaves (teas), raw or cooked whole fruit, berries and vegetables, nuts (e.g. kola nuts) the skins of fruit, fruit flesh (e.g. orange, prune, tangerine, grapefruit, grape), fruit rind (e.g. citrus fruits), peel, pips, cones (e.g. hops), seeds (e.g. cocoa beans; coffee beans; *Silybum marianum*) or stones, bark, buds (e.g. *Syzygium aromaticum*), flowers (e.g. cruciferous vegetables), roots, rhizomes and tubers (e.g. *Curcuma longa, Taraxacum officinale, Arctium lappa, Glycyrrhiza glabra, Zingiber officinalis*), stalks, and so on. Grape seed extract is one preferred antioxidant-rich source (b), being rich in proanthocyanidins. Grape skin and grape juice (or red wine extract), maritime pine bark, apples, plums, cherries, red cabbage, wolfberry, hawthorn berry, bilberry, huckleberry, cranberry, elderberry and blueberry and other fruit and vegetables with red, blue or purple pigmentation are other sources of proanthocyanidins. Vegetables which are rich in polyphenols include peppers (e.g. chilli peppers), spinach, broccoli, brussels sprouts, cabbage, kale, radishes, turnip and watercress. Extracts made from fruits and vegetables may have the advantage of providing both water-soluble vitamins (C and B complex) and polyphenols.

Interestingly, when grape seed extract and green tea extract were used in combination as antioxidant component (b) of the composition, the synergy with δ-tocols was reduced, when compared with green tea extract alone. Therefore, for optimal efficacy it is preferred that when green tea or extracts thereof are used as antioxidant source (b), extracts from any part of the grape fruit are omitted from the composition, and vice versa. Diminution of the synergistic effect may be a common occurrence when different sources of polyphenols are used in combination. Therefore, in general it is preferred that a single polyphenolic antioxidant source is present in the composition.

A unit dosage of the composition of the invention preferably comprises 1 mg to 500 mg polyphenols as antioxidant (b), in pure form or in an extract. Daily doses are suitably at least 1 mg, preferably 10 mg to 2000 mg, more preferably 100 mg to 1000 mg, and most preferably 250 mg to 700 mg.

In the composition of the invention the polyphenolic antioxidant source (b) is ideally present in equal weight (or concentration) or in weight excess (concentration excess) relative to the total tocol content of the composition, for example in a weight ratio of at least 1:1, preferably at least 1.5:1, more preferably at least 3:1, and most preferably at least 6:1.

Preferably the dry weight ratio of polyphenols to δ-tocols in the composition of the invention is in the range 1:1 to 200:1, more preferably 10:1 to 100:1, and most preferably 25:1 to 50:1.

In a preferred embodiment, the composition of the invention comprises a source of δ-tocol(s), in combination with one or more tea catechins, or tea (e.g. green tea or Pu Erh tea) or extracts thereof or mixtures thereof as antioxidant source (b). An appropriate source of δ-tocol(s) is a mix of concentrated tocopherols, such as that sold under the name of Covi-Ox™T-30 P (Cognis GmbH).

When δ-tocotrienol is the sole δ-tocol in the composition of the invention, antioxidant source (b) may comprise citrus flavonoids, but will in addition comprise other polyphenol(s).

Without wishing to be bound by theory, one possible explanation for the synergy observed using the compositions of this invention is that there is a cascade of redox cycles occurring in the serum. According to this theory, oxidation of endogenous α-tocopherol in the LDL complexes spares oxidation of LDL. Other tocols, especially δ-tocols, regenerate α-tocopherol at the expense of being oxidised themselves. Oxidised tocols may be recycled by polyphenolic antioxidants or their metabolites, and only when these antioxidants are exhausted, after an extended lag phase, does irreversible LDL oxidation start to occur.

Ascorbic acid, a known water-soluble antioxidant, has been postulated to recycle oxidized α-tocopherol in the LDL complexes. However, when ascorbic acid was tested in our in vitro assay, it was found not to have synergistic antioxidant properties when used in combination with TRF or purified δ-tocol. The same lack of synergy was observed with N-acetylcysteine, another well-recognized water-soluble antioxidant, and with α-lipoic acid, which is a fat-soluble antioxidant. None of these three antioxidants is polyphenolic, suggesting that the synergy is related to the presence of polyphenols in antioxidant agent (b).

The observation that delta tocols are better synergistic partners than any of the other tocol isomers suggests that the single methyl group on the phenol ring of the delta tocols is an important factor in this activity. If the recycling theory is correct, the implication is that the chemistry of the delta tocols allows them to reduce LDL α-tocopherol, or to be reduced by water-soluble antioxidants, in a more efficient manner than other tocols, or to undergo more redox cycles.

The antioxidant activity of α-tocopherol is not restricted to prevention of LDL oxidation, and it is generally known as a protective vitamin for lipids, and particularly membrane phospholipids. Therefore, the composition of the invention can be used to support and supplement endogenous α-tocopherol antioxidant activity in diverse sites and tissues around the body. The composition can be administered in nutritional, pharmaceutical or cosmetic form. Although enteral administration (especially oral) is preferred, topical application is also envisaged, whether as a pharmaceutical salve or as a skin lotion or cosmetic.

Preferably, components (a) and (b) are provided together in pharmaceutical form or as a dietary supplement, in combination with a pharmaceutically acceptable carrier. As an alternative, each component can be provided separately, e.g. in kit form, for separate, simultaneous or sequential administration. The pharmaceuticals or supplements are compositions for enteral (oral, nasal, or rectal), parenteral or topical administration, and can be in liquid or solid form.

Typical formulations will comprise (in % by weight) for example, from 0.001% to 100%, preferably about 0.1% to 50% by weight of each of active ingredients (a) and (b). Optionally the only active antioxidant components of the pharmaceutical or dietary supplement are tocol source (a) and antioxidant source (b). In some cases the tocol source (a) and antioxidant source (b) together constitute >10%, preferably >25%, and more preferably >50% by weight of the supplement;

Pharmaceutical compositions and dietary supplements can be produced in the form of hard or soft (gel) capsules, tablets, dragees, sachets, powders, lozenges, syrups, liquid suspensions, emulsions and solutions in convenient dosage forms.

Oral pharmaceutical or dietary supplement forms can be made by conventional compounding procedures known in the pharmaceutical art, that is, by mixing the active substances together with edible pharmaceutically acceptable solid or liquid carriers and/or excipients, e.g. fillers such as cellulose, lactose, sucrose, mannitol, sorbitol, and calcium phosphates and binders, and binders such as starch, gelatin, tragacanth, methylcellulose and/or polyvinylpyrrolidone (PVP). Optional additives include lubricants and flow conditioners (e.g. silicic acid, silicon dioxide, talc, stearic acid, magnesium/calcium stearates, polyethylene glycol (PEG) diluents, disintegrating agents (e.g. starch, carboxymethyl starch, cross-linked PVP, agar, alginic acid and alginates) colouring agents, flavouring agents, and melting agents. Dragée cores are provided with suitable, optionally enteric, coatings, there being used inter alia concentrated sugar solutions which may contain gum arabic, talc, PVP, PEG and/or titanium dioxide, or coating solutions in suitable organic solvents or solvent mixtures or, for the preparation of enteric coatings, solutions of suitable cellulose preparations, such as acetylcellulose phthalate or hydroxypropylmethylcellulose phthalate. Dyes or pigments may be added to the tablets or dragee coatings, for example for identification purposes or to indicate different doses of active ingredient.

Other orally administrable pharmaceutical compositions are hard gelatin capsules and also soft, sealed capsules consisting of gelatin and a plasticiser, such as glycerol or sorbitol. The hard gelatin capsules may comprise the active ingredient in the form of granules, for example in admixture with fillers, such as lactose, binders, glidants and, if desired, stabilisers. In soft capsules the active ingredients are preferably dissolved or suspended in suitable liquids, such as fatty oils, paraffin oil or liquid polyethylene glycols; it is likewise possible to add stabilisers.

Since the composition comprises hydrophilic and hydrophobic compounds a conventional emulsifier or surfactant may be employed to disperse the active ingredients uniformly within the end-product. Optionally, the hydrophobic tocols can be encapsulated in vesicles or micelles for incorporation into low-fat or water-based formulations. One method of preparing spray-dried powders containing tocotrienols for compression moulding is described in WO 00/27393 and is incorporated herein by reference. Where fats or oils are used as solvents, the water-soluble polyphenolic antioxidant may need to be treated to ensure dispersion, for example by ensuring the particle size is small, and/or by preparing an emulsion using a surfactant having a HLB (Hydrophilicity-Lipophilicity Balance) below 10.

When the composition of the invention is externally applied for cosmetic, hair care or skin care/skin protective purposes, it can be in the form of a cream, gel, ointment, solid stick, lotion or a solution, optionally together with emulsifiers. Typical compositions include lotions containing water and/or alcohols and emollients such as hydrocarbon oils and waxes, silicone oils, vegetable, animal or marine fats or oils, glyceride derivatives, fatty acids or fatty acid esters, alcohol or alcohol ethers, lanolin and derivatives, polyhydric alcohols or esters, wax esters, sterols, phospholipids and the like. Conventional water-insoluble or aqueous bases for ointments and creams may be used: e.g. fluid paraffin, petrolatum, wool wax, oleyl oleate, and the like. Cetylstearylalcohol and other emulsifying alcohols may be employed, as can non-alcohol emulsifiers such as Tween 20, Tween 80, and lecithin. If desired, a compound that reduces penetration of, or absorbs, UV radiation can be included in the composition, some examples being PABA, $TiO_2$, $ZnO_2$. A representative topical preparation will contain 0.1 to 20% by weight tocols, and at least an equivalent amount by weight of an antioxidant source (b).

The synergistic compositions of the invention can readily be incorporated into nutritional formulations, typically nutraceuticals or functional food and beverage products. For example, a δ-tocol source can be added to a familiar food product which is naturally rich in polyphenols, some examples being: green tea, herbal teas, coffee, cocoa, grape juice, elderberry juice, citrus juices, berry juices, red wine, beer, and chocolate. Alternatively, purified polyphenols or a source of polyphenols are added to a conventional food or beverage product which is rich in δ-tocols, such as cooking oils, margarines, whole grains, cereals and wholemeal products. Suitable product formats include yellow fat spreads, salad dressings, muesli, granola, muesli bars, crackers, biscuits, and cookies. Another option is to incorporate sources of both synergistic partners in a type of food or beverage which is low in endogenous polyphenols and δ-tocols, such as dairy products (cheese, butter, milk, milk-shakes, yogurt, smoothies, ice-cream, cream) and confectioneries (candies, chewing-gum, desserts, non-dairy toppings, sorbets, icings etc.). In general, food and beverage products of the invention will comprise nutritional quantities of one or more of carbohydrates, protein, fibre and fat.

The polyphenol content of a finished liquid product (drink) will normally lie in the range of about 0.01 to 1% by weight of the product, preferably 0.025 to 0.5% by weight. In a solid product (a food or reconstitutable drink powder) the usual range for polyphenol content is 0.05% to 5%, preferably 0.1 to 2%, by weight.

Edible or drinkable products of the invention will generally contain 0.001 to 0.5%, preferably 0.01% to 0.25% by weight of the finished product of δ-tocol source (a).

The beverage compositions of the present invention may be manufactured and sold for consumption by the consumer in the form of a syrup, an aqueous concentrate, a dry powder, or (effervescent) granules which are diluted with water to yield a beverage, or as a tablet to be taken with water.

Food and drink products containing the combination of δ-tocol source (a) and antioxidant source (b) are not only attractive to the consumer for their associated health benefits, but also have the advantageous characteristic of having a long shelf-life due to their potent antioxidant content. Accordingly, there may be no necessity to add artificial preservatives to the food and drink products of the invention, or at any rate amounts of these additives may be kept to a minimum. Fat- and oil-containing food products are particularly vulnerable to spoiling through the development of rancidity, and are therefore prime targets for inclusion of the synergistic antioxidant composition of the invention, optionally in conjunction with α-tocopherol.

If desired, other active ingredients may be combined with the toco/antioxidant source (b) composition of the invention. Particularly preferred are any natural ingredient or medicament known to have a beneficial effect in lowering cholesterol levels or in combating heart disease. It may, however, be advisable to exclude beta-carotene from the composition due to concerns about carcinogenicity. Other desirable components of the composition are factors that support or supplement free radical quenching, such as certain minerals, vitamins and metabolites.

The edible products of the invention optionally comprise conventional food additives, such as any of: emulsifiers, stabilizers, sweeteners, flavourings, colouring agents, preservatives, chelating agents, osmotic agents, acidulants, thickeners, texturisers, and so on.

The composition of the invention may be administered with beneficial effects to prevent, slow the progression of, or treat any disease associated with free radical damage, especially damage resulting in lipid peroxidation. This category includes CHD, cancer (e.g. sarcomas and carcinomas of the colon, pancreas, breast, ovary, prostate gland, lung etc.), rheumatism and inflammation, hepatitis, alcoholism, Alzheimer's disease, dementia, diabetes, multiple sclerosis, HIV and AIDS, collagen degradation, cataracts, macular degeneration, accelerated aging, neuropathies, myopathies, ischemia-reperfusion injury, haemorrhagic shock, gum disease, cold sores, psoriasis, eczema, seborrhea. The invention can also be applied to counteract the effects of formation of reactive oxygen species (ROS), whatever the cause, including that resulting from environmental pollution or irradiation, and from treatment with neoplastic drugs.

In particular, this new form of treatment can be applied to prevent or treat CHD and its underlying causes. Because of the direct connection between prevention of LDL oxidation and retardation of atherosclerosis, stroke patients and cardiac infarct patients, or those at risk of these conditions, will especially profit from treatment with the claimed compositions. Type 2 diabetics have an increased preponderance of small dense LDL, which predisposes to the oxidation of LDL, and in addition have lower levels of endogenous α-tocopherol. Therefore this patient group is a target group particularly well suited to treatment in accordance with the present method.

Ingestion of the composition of the invention can be employed as a cosmetic treatment method, in particular to counteract the development of wrinkles, delay skin aging, and improve the overall appearance of skin, eyes and hair.

Smokers and sunbathers are particularly vulnerable to cancer and aging of the skin and other tissues as a consequence of free radical generation. To some extent they can compensate by maintaining an elevated intake of antioxidants in their diets, which is easily achievable by consuming the composition of the present invention.

Exercise is believed to trigger an increase in free radical production by an increase in oxygen generation in the mitochondrial electron transport chain or by an increase in metal-catalysed free radical production due to mechanical and morphological damage to muscles. It has been reported that lipid and protein oxidation is a consequence of extended exercise. The present invention provides a convenient method for avoiding or minimizing oxidation damage consequent upon physical activity.

In accordance with the present invention, a method of preventing or treating a medical condition caused by generation of free radicals in the mammalian body comprises administering, to a person in need of such treatment, an effective amount of a combination of (a) a tocol source comprising δ-tocols and (b) an antioxidant source comprising polyphenols, wherein δ-tocols preferably constitute greater than 2% by weight of the source (a). According to another aspect of the invention, a method of preventing oxidative tissue damage in a mammal due to physical activity comprises administration of a tocol source comprising δ-tocols (preferably greater than 2% by weight δ-tocol) in combination with a polyphenol-containing antioxidant source.

EXAMPLES

Oxidation of LDL In Vitro

Plasma was obtained from the blood of healthy male and female volunteers and was frozen. After thawing, the plasma was adjusted to a density of 1.057 with solid KBr, and overlaid with 0.15M NaCl (density=1.006 kg/l). Tubes were then centrifuged at 400 000 g at 15° C. for 2 hours. The top fraction (chylomicrons+VLDL) was removed. To isolate the LDL fraction the remaining plasma was adjusted to a density of 1.063 kg/l with solid KBr and the tube was filled with KBr solution (density=1.063). After centrifugation at 400 000 g at 15° C. for 2 hours, the LDL fraction floating on the top was collected.

The LDL fraction contained between about 300-700 μg/ml proteins. The fractions were supplemented with ethanolic solutions containing various extracts or with the same volume of pure ethanol (control). Oxidation was initiated by adding freshly-prepared CuSO4 solution (25 μmol/l final concentration) at 37° C. The kinetics of the oxidation of lipoprotein was determined by continuously monitoring the change in absorbance at 234 nm (at 37° C.) on a UV/VIS spectrophotometer, which correlates with the increase in conjugated diene absorbance. The effective concentration of active agent at which 50% of the response was observed is defined as the $EC_{50}$.

The time required for the formation of diene is defined as the lag phase. The longer the lag phase the better the protection of LDL against oxidation. Since it is believed that LDL oxidation contributes to the development of atherosclerosis, and correlates with the risk of developing coronary heart disease (CHD) any factor which delays the oxidation of LDL in the in vitro assay is a strong candidate for use in a medicament, food or dietary supplement for treating or preventing these medical conditions.

Concentration-response curves for the LDL oxidation assay were plotted separately for each of the tocol preparations, and for the water-soluble antioxidant preparations (see FIGS. 1 to 5). In each experiment, the tocotrienol content of the tocol preparations (TRF) was standardised to 0.05 or 0.1 μg/ml.

As can be seen in FIG. 1, green tea extracts (GT, Greenselect®) and grape seed extract (GS, Leucoselect®), both supplied by Indena, are at least equal in antioxidant potency to tocols (in this case palm oil TRF "Gold Tri-E" containing 7 wt % δ-tocotrienol and supplied by Sugro, "S") in this assay (i.e. they have lower $EC_{50}$ values). Particular combinations of these two classes of antioxidants were tested in the same assay. Additive antioxidant effects would have been indicated by a lag time corresponding to the addition product of the lag times of the individual components. In fact, synergy was observed, i.e. the lag time achieved with the combination of GT/TRF and GS/TRF was significantly longer than the sum of the individual lag times.

(Sugro TRF was used at a tocotrienols equivalent concentration of 0.1 μg/ml. Green tea and grape seed extracts were used at a concentration of 0.4 μg/ml, except in the case where green tea and grape seed were used together, when each was used at a concentration of 0.2 μg/ml.)

Figure 2:
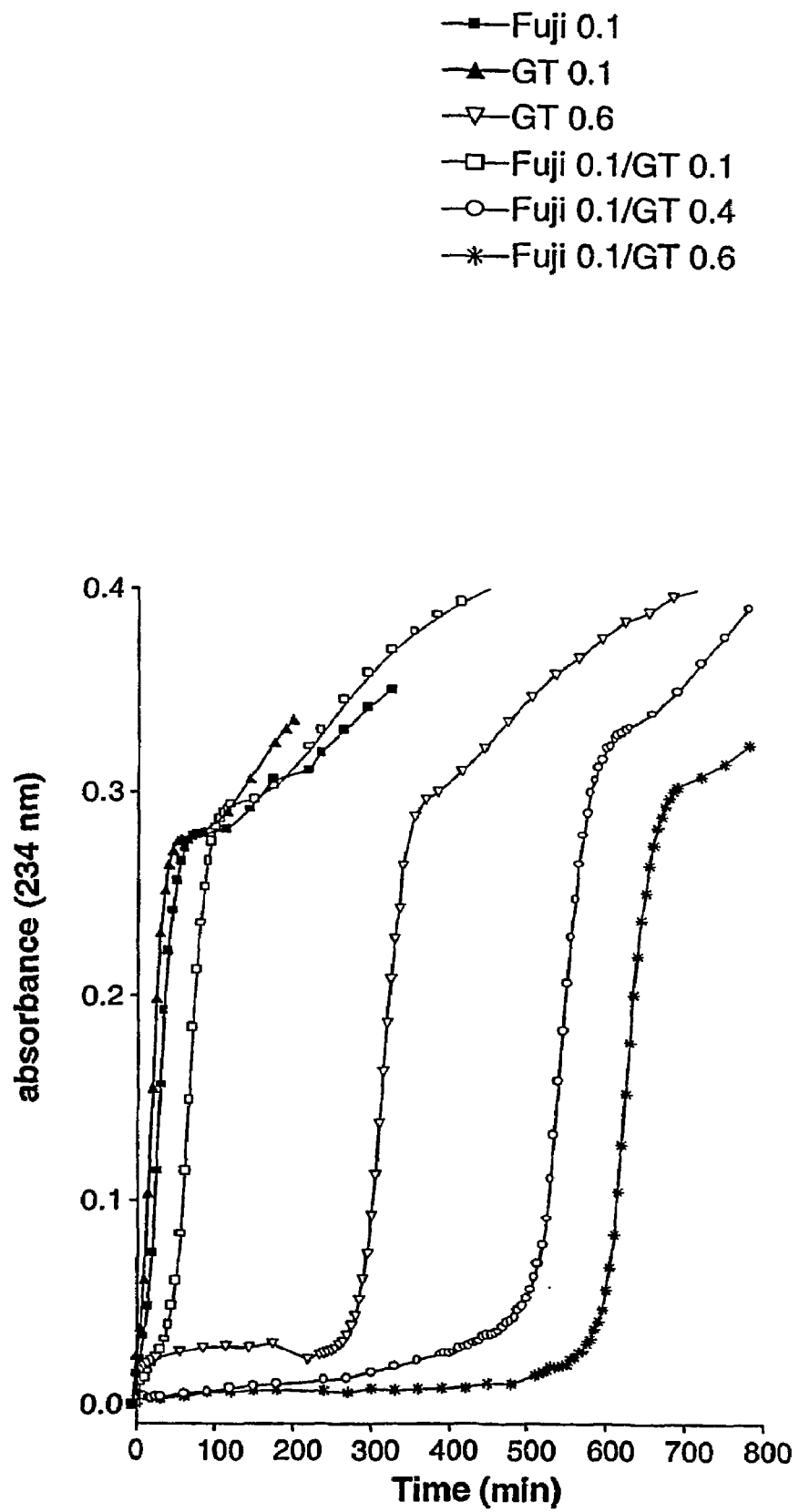
FIG. 2 is a graph showing synergism in the LDL oxidation assay at different concentration ratios of green tea extract (GT):TRF (Fuji).

The results shown in FIG. 2 demonstrate that synergy between green tea extract (GT) and TRF (Fuji, approx. 9 wt % δ-tocotrienol) is demonstrable at concentration ratios of 1:1 and higher. In the experiments Fuji TRF was used at a tocotrienols equivalent concentration of 0.1 μg/ml, and green tea extract was used at a concentration of 0.1, 0.4 or 0.6 μg/ml.

Figure 3:
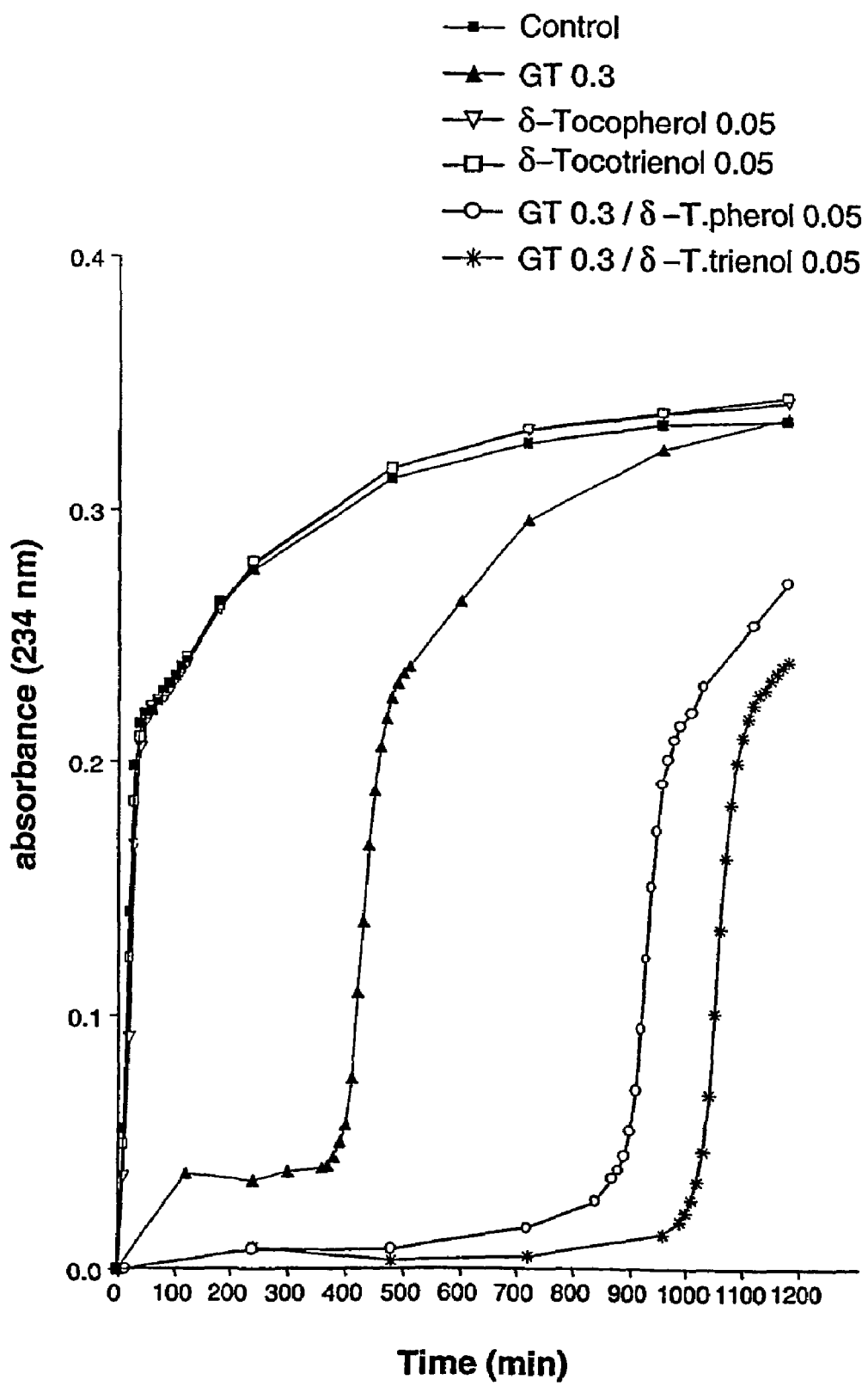
FIG. 3 is a graph comparing the antioxidant effects of pure δ-tocotrienol and δ-tocopherol in combination with green tea extract (GT) in the LDL oxidation assay.

FIG. 3 illustrates that purified δ-tocols, when combined with green tea extract (GT), show synergistic antioxidant interactions in the LDL oxidation assay. Here the synergistic properties of this combination result in a striking extension to the lag time as compared with the sum of the individual component lag times. The lag phase observed with purified δ-tocols was also significantly and consistently lengthened in comparison with that observed using other tocol isomers in combination with green tea extract under otherwise identical conditions. δ-tocols were used at a concentration of 0.05 μg/ml, and green tea at 0.3 μg/ml.

Figure 4:
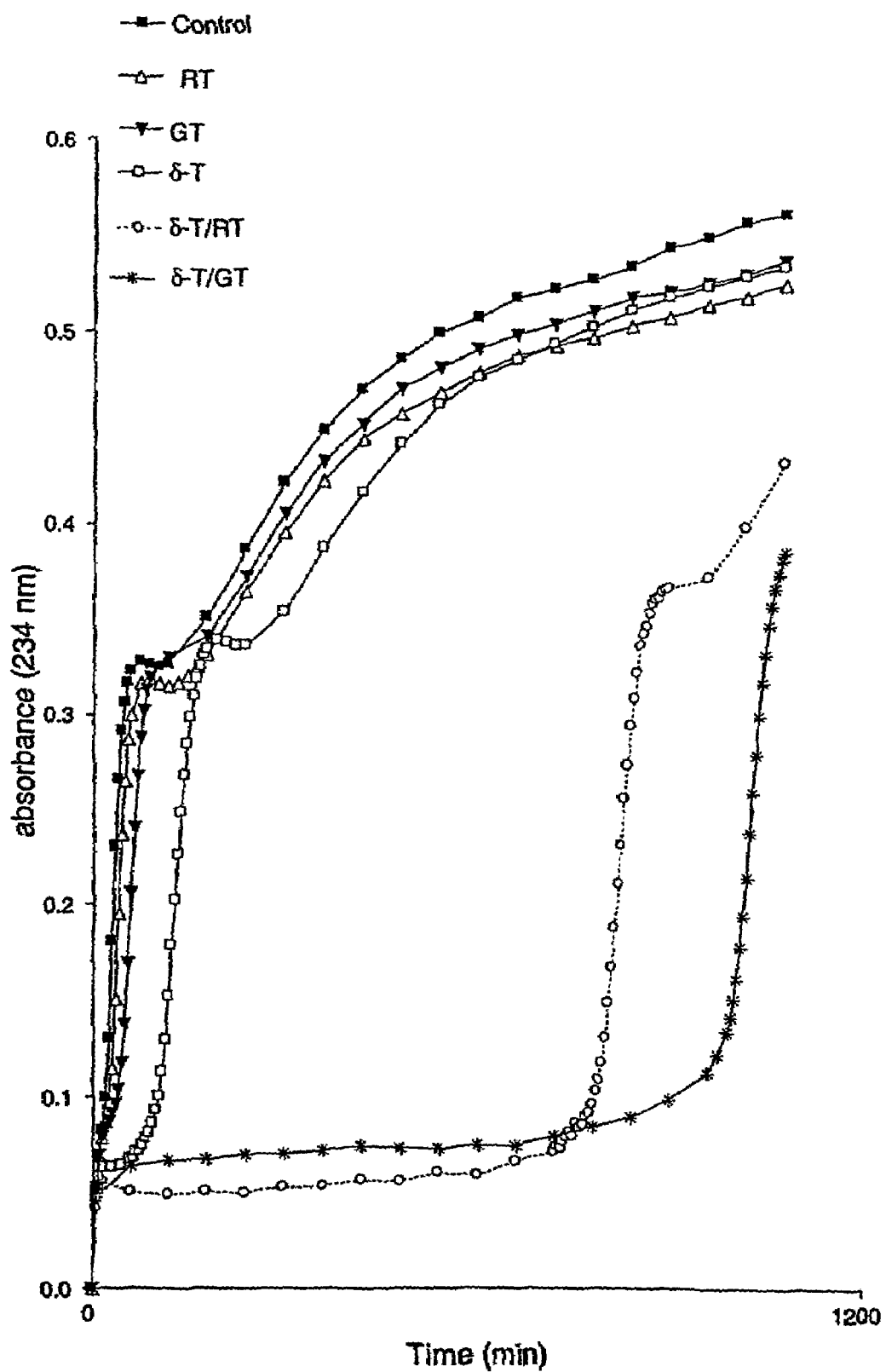
FIG. 4 compares the antioxidant effects in the LDL oxidation assay of green tea (GT) and Pu Erh red tea (RT) when tested in conjunction with δ-tocotrienol (δ-T).

FIG. 4 shows that both green tea (GT) and Pu Erh red tea (RT) are capable of inducing an extended LDL oxidation lag phase when combined with δ-tocotrienol (δ-T). The teas were used at a concentration of 0.3 μg/ml, and &tocotrienol was used at a concentration of 0.1 μg/ml in the assay.

Figure 5:
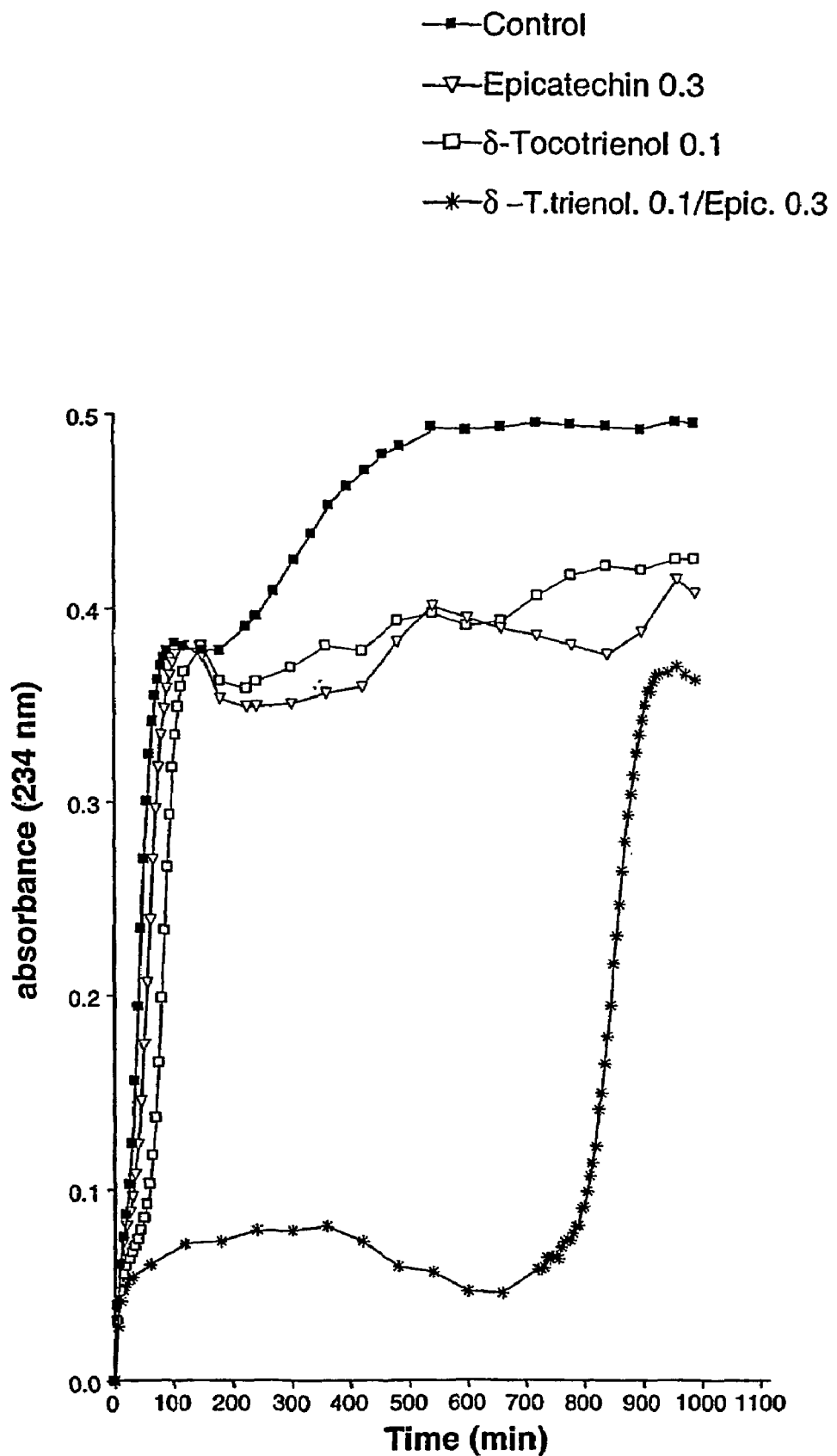
FIG. 5 demonstrates the effects of using pure epicatechin as a synergistic partner with δ-tocotrienol in the LDL oxidation assay.

In FIG. 5 it is shown that pure catechin (epicatechin from Sigma) can substitute for green tea extract as a polyphenolic antioxidant partner with δ-tocotrienol in the LDL oxidation assay. δ-tocotrienol was used at a concentration of 0.1 μg/ml and epicatechin was used at 0.3 μg/ml.

The invention claimed is:

1. A composition comprising:
    (a) a source of δ-tocol comprising greater than 2% by weight said δ-tocol; and
    (b) polyphenols,
    wherein a dry weight ratio of said polyphenols to said δ-tocol is in the range of 25:1 to 50:1, and said δ-tocol comprises δ-tocopherol when said polyphenols comprises citrus flavonoids, and wherein said composition is substantially free of α-tocopherol.
2. A composition according to claim 1, which in a unit dosage comprises 0.5 to 50 mg δ-tocol.
3. A composition comprising in a daily dosage:
    (a) at least 5 mg δ-tocol selected from the group consisting of δ-tocopherol, δ-tocotrienol and mixtures thereof; and
    (b) polyphenols,
    wherein a dry weight ratio of said polyphenols to said δ-tocol is in the range of 25:1 to 50:1 , and wherein said composition is substantially free of α-tocopherol.
4. A composition comprising in a daily dosage:
    (a) at least 5 mg of δ-tocol selected from the group consisting of δ-tocopherol, δ-tocotrienol and mixtures thereof; and
    (b) polyphenols other than citrus flavonoids,
    wherein a dry weight ratio of said polyphenols to said δ-tocol is in the range of 25:1 to 50:1, and wherein said composition is substantially free of α-tocopherol.
5. The composition according to claim 1, further comprising a catechin.
6. The composition according to claim 1, further comprising α-tocopherol, wherein a weight ratio of δ-tocol to α-tocopherol is greater than 0.65.
7. The composition according to claim 1, wherein δ-tocol is a Tocotrienol Rich Fraction (TRF) source selected from the group consisting of palm oil or rice bran oil and a blend of tocopherols, and said polyphenols is selected from the group consisting of green tea, Pu Erh tea, extracts thereof and mixtures thereof.
8. The composition according to claim 1, which is substantially free of tocols other than δ-tocols.
9. The composition according to claim 1, wherein an antioxidant property of the composition is greater in the case that said polyphenols consist of a single polyphenolic antioxidant source than in the case that said polyphenols include more than one polyphenolic antioxidant source.
10. The composition according to claim 1, further comprising a nutritionally quantity of a carbohydrate, a fat, a fiber or a protein.
11. The composition according to claim 1, further a pharmaceutically acceptable carrier.
12. The composition according to claim 11, further comprising antioxidants consisting essentially of said δ-tocol and said polyphenols.
13. A kit comprising:
    (a) a source of δ-tocol preferably comprising greater than 2% by weight δ-tocol; and
    (b) an antioxidant source comprising polyphenols,
    for separate, sequential or simultaneous administration,
    wherein a dry weight ratio of said polyphenols to said δ-tocol is in the range of 25:1 to 50:1, wherein said δ-tocol is selected from the group consisting of δ-tocopherol, δ-tocotrienol and mixtures thereof, and wherein said kit is substantially free of α-tocopherol.
14. The composition according to claim 1, further a cosmetically acceptable carrier.
15. A method of treating a medical condition caused by the generation of free radicals comprising the step of administering to a person in need of such treatment an effective amount of a source of δ-tocol comprising greater than 2% by weight said δ-tocol and polyphenols, wherein a dry weight ratio of said polyphenols to said δ-tocol is in the range of 25:1 to 50:1, and said δ-tocol comprises δ-tocopherol when said polyphenols comprises citrus flavonoids, and wherein administration is substantially free of α-tocopherol.

16. The method of claim 15, wherein said medical condition is selected from the group consisting of arteriosclerosis, rheumatism and cancer.

17. The method of claim 15, wherein said medical condition is caused by physical activity, sun exposure or smoking.

18. A method of preventing spoilage in a food or beverage product comprising the step of using a composition comprising a source of δ-tocol preferably comprising greater than 2% by weight δ-tocol and an antioxidant source comprising polyphenols as a preservative wherein a dry weight ratio of said polyphenols to said δ-tocol is in the range of 25:1 to 50:1, wherein said δ-tocol is selected from the group consisting of δ-tocopherol, δ-tocotrienol and mixtures thereof, and wherein said composition is substantially free of α-tocopherol.

\* \* \* \* \*